(12) United States Patent
Thiem

(10) Patent No.: US 7,368,081 B2
(45) Date of Patent: May 6, 2008

(54) SYSTEM FOR STAINING AND COVERSLIPPING SPECIMEN SLIDES

(75) Inventor: Stefan Thiem, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 11/564,436

(22) Filed: Nov. 29, 2006

(65) Prior Publication Data
US 2007/0098599 A1 May 3, 2007

Related U.S. Application Data

(63) Continuation of application No. 10/230,481, filed on Aug. 29, 2002, now Pat. No. 7,153,474.

(30) Foreign Application Priority Data
Sep. 12, 2001 (DE) ................. 101 44 989

(51) Int. Cl.
B32B 5/02 (2006.01)
(52) U.S. Cl. ............... 422/63; 422/65; 422/99; 422/100; 422/101; 436/180
(58) Field of Classification Search ............ 422/63–65, 422/99–101; 436/180
See application file for complete search history.

(56) References Cited

U.S. PATENT DOCUMENTS 4,190,472 A  2/1980  Slonicki
4,537,648 A  8/1985  Shiino et al.
5,601,650 A  2/1997  Goldbecker et al.
5,895,628 A * 4/1999  Heid et al. .................... 422/65
6,076,583 A  6/2000  Edwards
6,626,224 B1  9/2003  Ljungmann
7,153,474 B2 * 12/2006  Thiem ......................... 422/63

FOREIGN PATENT DOCUMENTS

| JP | 61-176435 U1 | 11/1986 |
|---|---|---|
| JP | 4-318441 A1 | 11/1992 |
| JP | 7-333123 A1 | 12/1995 |
| WO | 95/20176 A1 | 7/1995 |
| WO | WO-97/03827 A1 | 2/1997 |
| WO | WO-00/37986 A1 | 6/2000 |
| WO | 00/62035 A1 | 10/2000 |
| WO | WO0138848 A1 * | 11/2000 |

* cited by examiner

Primary Examiner—Jill Warden
Assistant Examiner—Jyoti Nagpaul
(74) Attorney, Agent, or Firm—Hodgson Russ LLP

(57) ABSTRACT

A system (100) for staining and coverslipping specimen slides comprises a first part (the stainer (1)) and a second part (the coverslipper (20)). A transport device (5), with which racks (4) carrying specimen slides are transferred directly from the stainer (1) into the coverslipper (20), is provided in the stainer (1).

1 Claim, 3 Drawing Sheets

SYSTEM FOR STAINING AND COVERSLIPPING SPECIMEN SLIDES

CROSS REFERENCE TO RELATED APPLICATIONS

This application is a continuation of U.S. application Ser. No. 10/230,481 filed Aug. 29, 2002, now U.S. Pat. No. 7,153,474 which claims priority of the German patent application 101 44 989.5 filed Sep. 12, 2001 which is incorporated by reference herein.

FIELD OF THE INVENTION

The invention concerns a system for staining and coverslipping specimen slides, having a first part that comprises a stainer in which a transport device is provided for handling racks with specimen slides, and having a second part that comprises a coverslipper.

BACKGROUND OF THE INVENTION

WO 95/20176 discloses an instrument for automatic deposition of coverslips. The pickup head possesses suction cups, facing outward from the longitudinal axis of the pickup head, to which a vacuum can be applied individually. A piston that is mechanically preloaded downward with a spring is provided between the suction cups. In order to pick up a coverslip, the pickup head is pressed onto the coverslip stack and until the suction cups are in contact with the topmost coverslip. The adhesion between the topmost coverslip and the coverslips below it is overcome by means of a shearing motion. The specimen slides that are to be equipped with coverslips are deposited in a drawer. This does not result in any automation of the apparatus, since the user him- or herself must reload specimen slides.

The automatic stainer and coverslipper are two separate units. According to the existing art, after the staining operation the specimen slides needed to be manually removed from the stainer and inserted into the coverslipper in order to start the process of covering them with coverslips (see Leica brochure CV 5000). Despite the automation of the individual units, manual loading of the coverslipper is necessary. Smooth operation requires that laboratory personnel occupy themselves, at very short intervals of a few minutes, with removing racks from the stainer and loading the coverslipper.

SUMMARY OF THE INVENTION

It is the object of the invention to create a system intended to guarantee the greatest possible degree of automation in the handling of specimen slides, in which context the intervention of an operator during staining and subsequent coverslipping of the specimen slides is to be minimized.

This object is achieved by means of a system which is characterized in that the transport device transfers racks with specimen slides from the stainer directly into the coverslipper.

The advantage of the system according to the present invention is that the transport device present in the stainer transfers racks with specimen slides from the stainer directly into the coverslipper. This eliminates the interposition of a further device which first picks up the racks before they are then transferred by the further device into the coverslipper. This configuration is economical. In addition, the system will be less affected by system faults because the rack with the specimen slides does not need to pass through transfer positions. In a particular embodiment, the system for staining and coverslipping specimen slides is configured in such a way that the stainer and the coverslipper are each surrounded by an individual housing. In addition, the stainer and the coverslipper are equipped with a pivotable cover. The stainer and coverslipper thus each constitute a separately closed system.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
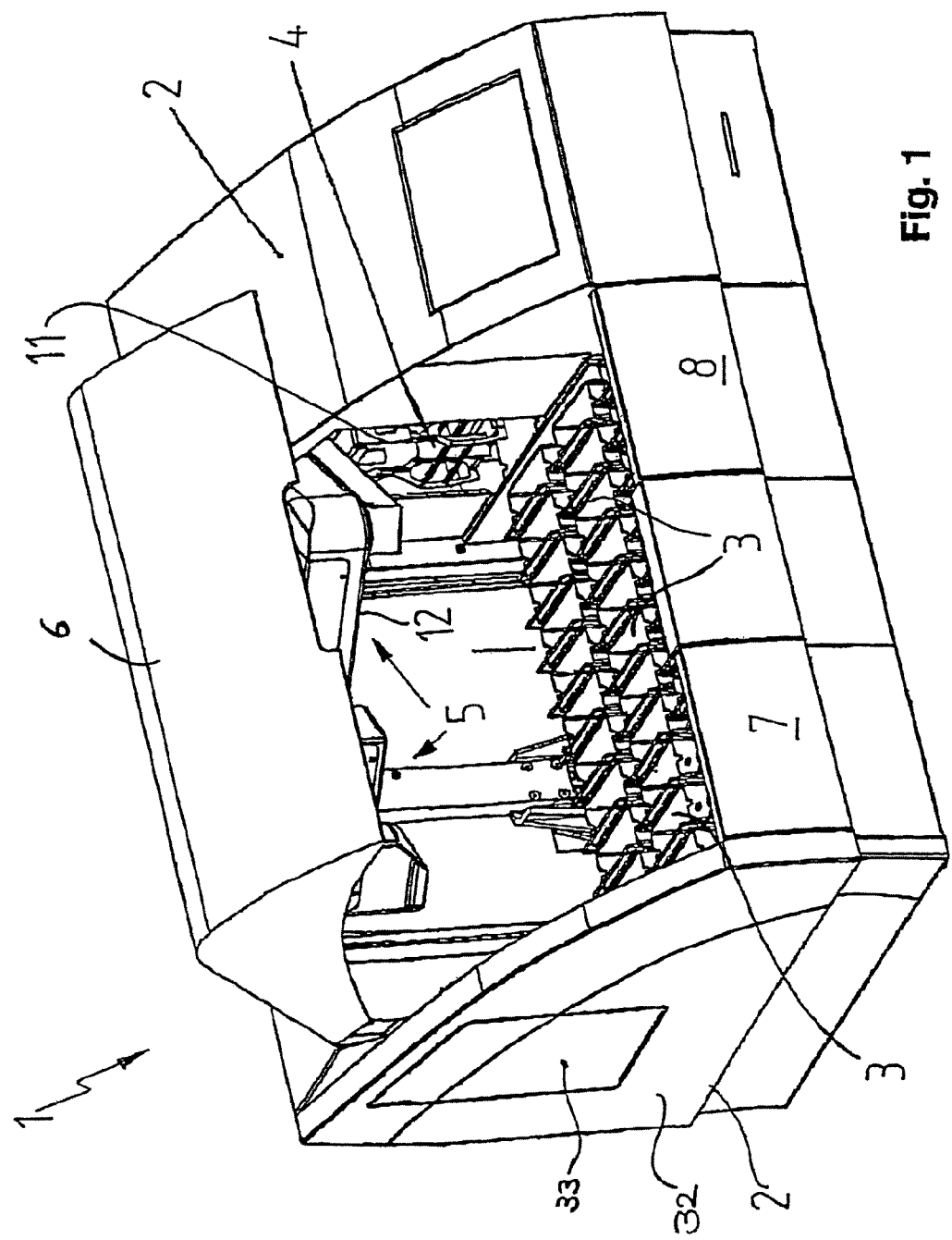
FIG. 1 schematically depicts an exemplary embodiment of a stainer in which the loading station is embodied as a drawer.

It is evident from FIG. 1 that a transport device 5, which delivers racks 4 carrying specimen slides (not depicted) to the various processing stations 3, is provided in stainer 1. Stainer 1 comprises a housing 2 as well as processing stations 3 arranged in housing 2, said stations being configured as vessels for receiving racks 4 with specimen slides.

Also evident from FIG. 1 is a transport device 5, the latter serving to deliver racks 4 with the specimen slides into processing stations 3 or the vessels, and to take them out of processing stations 3 or the vessels. Cover 6 serving to cover stainer 1 is open to allow a view into stainer 1. Drawers 7, 8 for loading stainer 1 and for removing the treated specimens, or specimens slides carrying the treated specimens, are shown in the closed position.

Drawer 7 serves as a removal station for the removal of racks 4 from stainer 1. Racks 4 can thus be delivered manually by a user to a further processing operation.

A loading station 11 is also provided in stainer 1. Both loading station 11 and removal station 7 are reached via transport device 5. By means of transport device 5 it is thus possible to remove racks 4 carrying the specimen slides that are present in loading station 11 and deliver them to the actual processing stations 3. After the last processing station 3 in the process implemented in stainer 1, racks 4 with the specimen slides are transferred directly to a coverslipper 20 (see FIG. 2). The transfer is performed, with transport device 5, to coverslipper 20 that is downstream in this embodiment. In the embodiment depicted here, stainer 1 and coverslipper 20 are each surrounded by a housing 2 and 22, accessible from the outside via a respective cover 6 and 25. It is nevertheless self-evident for one skilled in the art also to configure a system 100 in such a way that stainer 1 and coverslipper 20 form one unit. Transport device 5 in stainer 1 would accordingly be configured so that racks 4 with the specimen slides are delivered directly into a transfer position (not depicted) associated with the coverslipper 20. The description below refers to a system in which coverslipper 20 and stainer 1 are each surrounded by a separate housing 22 and 2. This is not to be construed in any way, however, as a limitation of the invention.

In the exemplary embodiment selected here, transport device 5 is embodied to include a robot arm 12. An opening 33, through which racks 4 with specimen slides can be transferred to coverslipper 20, is configured in a side wall 32 of stainer 1.

Figure 2:
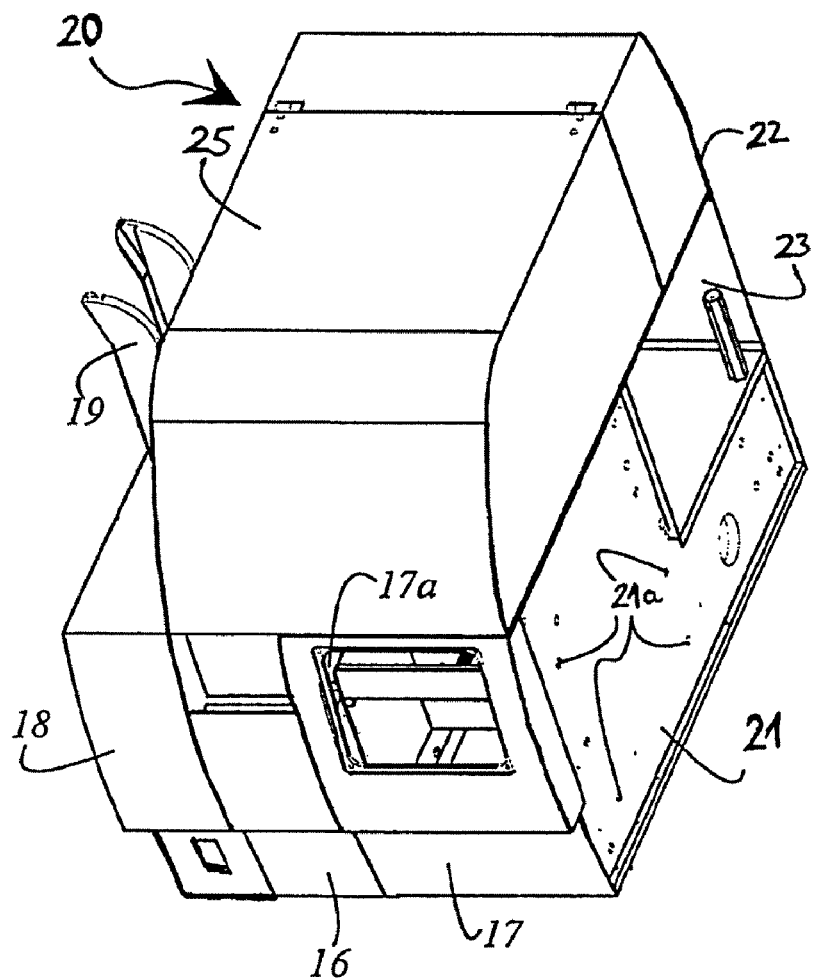
FIG. 2 schematically depicts an exemplary embodiment of a coverslipper.

FIG. 2 schematically depicts an exemplary embodiment of coverslipper 20. In this embodiment, coverslipper 20 also comprises a housing 22 that has on one side wall 21 several attachment elements 21*a* that coact with attachment elements 34 on the corresponding side wall 32 of stainer 1. Side wall 21 also has an opening 23 through which racks 4 with the specimen slides are delivered from stainer 1 into coverslipper 20. The interior of coverslipper 3 is covered with a pivotable cover 25. Front wall 26 of coverslipper 20 has a first drawer 17 in which a further opening 17*a*, into which a user interface (not depicted) can be inserted, is configured. Also provided in addition to first drawer 17 for the user interface and the access for the electronics of coverslipper 20 is a removal panel 18 by means of which the user also has access to the interior of coverslipper 20.

Also provided on coverslipper 20 is an output tray 19 for specimen slides equipped with coverslips.

Communication between coverslipper 20 and stainer 1 occurs as follows: stainer 1 queries whether it can place a rack 4 in coverslipper 20. The response from coverslipper 20 can be "yes" or "no." If "no," the query is repeated at periodic intervals. If "yes," the rack is put in place and a "rack transferred" message is generated. Coverslipper 20 responds "rack received." This procedure eliminates long waiting times for the rack in the transfer position. A quick transfer is advantageous because the specimen slides usually sit in a bath of solvent (often xylene), and wet specimen slides that were just recently stored in solvent exhibit considerably better flow behavior for the coverslip adhesive. It is particularly advantageous if a container with solvent, into which racks 4 with the specimen slides can be deposited, is also provided in coverslipper 20.

Figure 3:
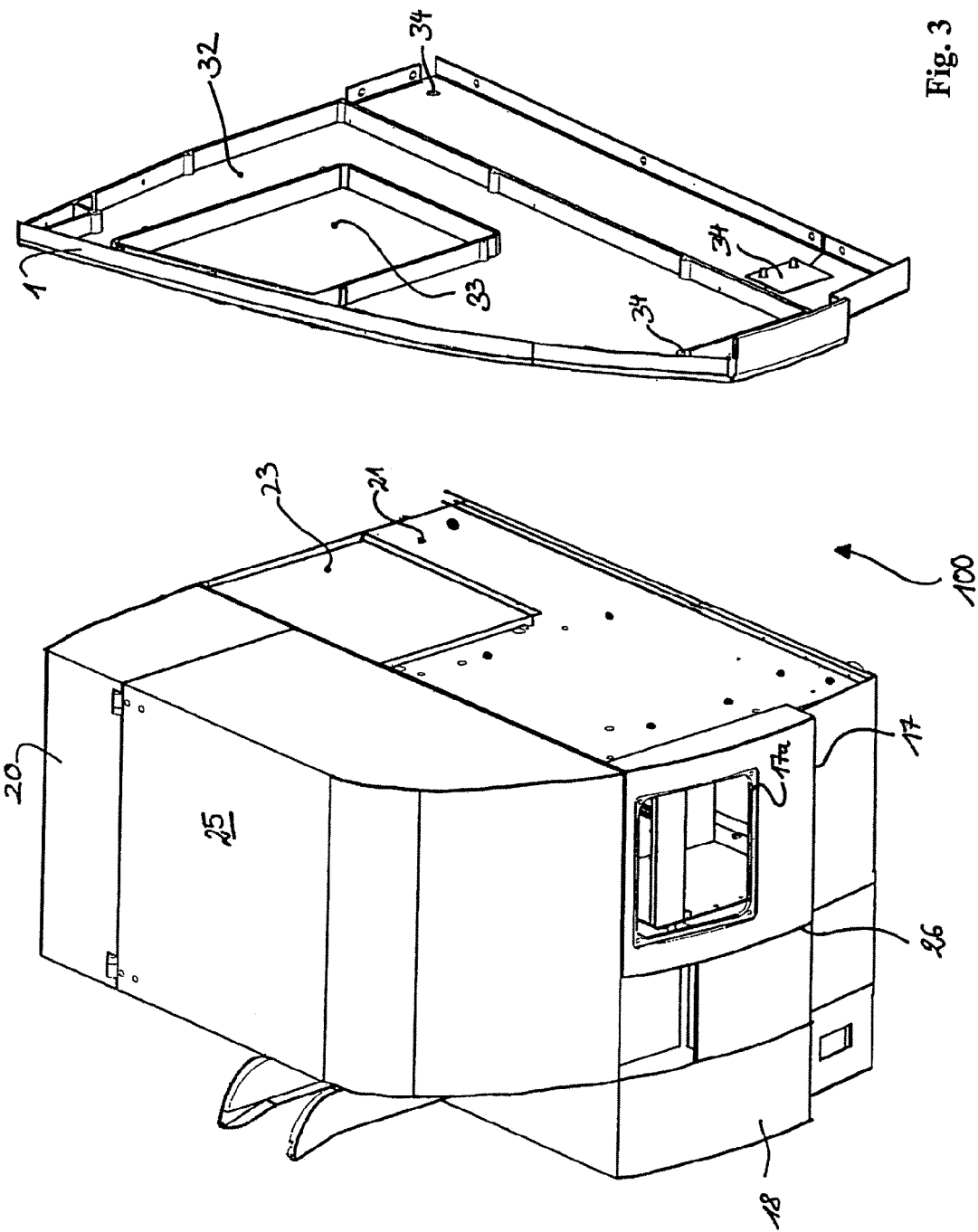
FIG. 3 schematically depicts a system according to the present invention, the individual elements being separated from one another and only one side wall of the stainer being depicted.

As depicted in FIG. 3, the elements of system 100 are shown separated from one another for better clarity. In operation, stainer 1 (only one side wall 32 shown here) and coverslipper 20 are connected to one another. Stainer 1 possesses lateral opening 33 through which transport device 5 of stainer 1 can pass. Specifically, transport device 5 is used on the one hand to accept racks 4 with specimen slides from other processing stations and to transfer racks 4 with specimen slides for transfer to coverslipper 20. Transport device 5 extends through opening 23 in side wall 21 of coverslipper 20. In system 100 according to the present invention, the individual elements are assembled together. Stainer 1 and coverslipper 20 are connected to one another and form a system 100 substantially closed off externally.

The invention has been described with reference to a particular exemplary embodiment. It is nevertheless self-evident that changes and modifications can be made without thereby leaving the range of protection of the claims below.

PARTS LIST

1 Stainer
 2 Housing
 3 Processing stations
 4 Racks
 5 Transport device
 6 Cover
 7 Drawers
 8 Drawers
 11 Loading station
 12 Robot arm
 17 First drawer
 17*a* Further opening
 18 Panel
 19 Output tray
 20 Coverslipper
 21 Side wall
 21*a* Attachment elements
 22 Housing of coverslipper
 23 Opening
 25 Cover
 26 Front wall
 32 Side wall
 33 Lateral opening
 34 Attachment element
 100 System

What is claimed is:

1. A method for assembling a system for staining and coverslipping specimen slides comprising the steps of:
   A) providing an automated stainer having a stainer housing;
   B) providing an automated coverslipper having a coverslipper housing;
   C) aligning a wall opening of the stainer housing opposite a wall opening of the coverslipper housing; and
   D) linking the stainer housing to the coverslipper housing to allow transfer of specimen slides from the stainer housing to the coverslipper housing through the aligned wall openings.

* * * * *